United States Patent [19]
Brimhall et al.

[11] Patent Number: 5,792,122
[45] Date of Patent: Aug. 11, 1998

[54] TELESCOPING NEEDLE SHIELD

[75] Inventors: Greg L. Brimhall, West Jordan; Charles W. Daugherty, Sandy, both of Utah; Floyd V. Edwards, Clarence, N.Y.

[73] Assignee: Becton Dickinson and Company, Franklin Lakes, N.J.

[21] Appl. No.: 903,686

[22] Filed: Jul. 31, 1997

Related U.S. Application Data

[63] Continuation of Ser. No. 682,479, Jul. 17, 1996, abandoned, which is a continuation of Ser. No. 501,604, Jul. 12, 1995, abandoned.

[51] Int. Cl.$^6$ .................................................. A61M 5/00
[52] U.S. Cl. .......................... 604/263; 604/164; 604/198
[58] Field of Search ........................... 604/263, 187, 604/110, 192, 198, 51, 158, 163, 164, 171

[56] References Cited

U.S. PATENT DOCUMENTS

| | | | |
|---|---|---|---|
| 3,867,937 | 2/1975 | Schwartz | 128/221 |
| 3,994,295 | 11/1976 | Wulft | 128/215 |
| 4,702,737 | 10/1987 | Pizzino | 604/191 |
| 4,725,267 | 2/1988 | Vaillancourt | 604/192 |
| 4,762,516 | 8/1988 | Luther et al. | 604/164 |
| 4,804,372 | 2/1989 | Laico et al. | 604/198 |
| 4,832,696 | 5/1989 | Luther et al. | 604/164 |
| 4,834,718 | 5/1989 | McDonald | 604/195 |
| 4,846,805 | 7/1989 | Sitar | 604/165 |
| 4,846,811 | 7/1989 | Vanderhoof | 604/263 |
| 4,892,521 | 1/1990 | Laico et al. | 604/192 |
| 4,897,083 | 1/1990 | Martell | 604/192 |
| 4,921,491 | 5/1990 | Champ | 604/199 |
| 4,935,013 | 6/1990 | Haber et al. | 604/192 |
| 4,936,930 | 6/1990 | Verlier | 604/110 |
| 4,944,725 | 7/1990 | McDonald | 604/164 |
| 4,944,728 | 7/1990 | Carrell et al. | 604/164 |
| 4,950,250 | 8/1990 | Haber et al. | 604/192 |
| 4,950,252 | 8/1990 | Luther et al. | 604/198 |
| 4,973,317 | 11/1990 | Bobrove | 604/198 |
| 4,978,344 | 12/1990 | Dombrowski et al. | 604/198 |
| 4,994,041 | 2/1991 | Dombrowski et al. | 604/164 |
| 5,011,479 | 4/1991 | Le et al. | 604/198 |
| 5,013,305 | 5/1991 | Opie et al. | 604/192 |
| 5,104,384 | 4/1992 | Parry | 604/192 |
| 5,181,524 | 1/1993 | Wanderer et al. | 128/764 |
| 5,219,338 | 6/1993 | Haworth | 664/198 |
| 5,242,416 | 9/1993 | Hutson | 604/192 |
| 5,273,540 | 12/1993 | Luther et al. | 604/110 |
| 5,295,975 | 3/1994 | Lockwood, Jr. | 604/198 |
| 5,304,136 | 4/1994 | Erskine et al. | 604/110 |
| 5,322,517 | 6/1994 | Sircom et al. | |
| 5,332,092 | 7/1994 | Fischer | 206/365 |
| 5,334,149 | 8/1994 | Nortman et al. | 604/110 |
| 5,336,199 | 8/1994 | Castillo et al. | 604/198 |
| 5,419,766 | 5/1995 | Chang et al. | 604/110 |
| 5,456,668 | 10/1995 | Ogle, II | 604/110 |
| 5,531,713 | 7/1996 | Mastronardi et al. | 604/263 |

FOREIGN PATENT DOCUMENTS

| | | |
|---|---|---|
| 0 554 841 A1 | 8/1993 | European Pat. Off. . |
| 0 576 302 A1 | 12/1993 | European Pat. Off. . |
| 0 578 367 A1 | 12/1994 | European Pat. Off. . |
| WO 91/01151 | 2/1991 | WIPO . |
| WO 94/13341 | 6/1994 | WIPO . |

*Primary Examiner*—John D. Yasko
*Attorney, Agent, or Firm*—Eric M. Lee

[57] ABSTRACT

A needle assembly is provided with a needle securely mounted to a needle hub. A shield assembly includes a plurality of telescoped tubes concentrically surrounding the needle. One of the telescoped tubes is securely connected to the needle hub. The other tubes in the assembly may be slid away from the needle hub. The tubes have combined lengths to enable complete shielding of the needle when the tubes are telescopingly extended. The distal-most tube, when the tubes are telescopingly extended, includes a tip guard which resiliently moves over the distal tip of the needle as the shield assembly is fully extended. The distal-most tube, when the tubes are telescopingly extended, of the shield assembly frictionally engages a catheter adapter to prevent withdrawal of the needle from the shield assembly until the tubes are fully telescopingly extended. As full shielding of the needle is reached, the shielded needle is separated from the catheter adapter.

14 Claims, 5 Drawing Sheets

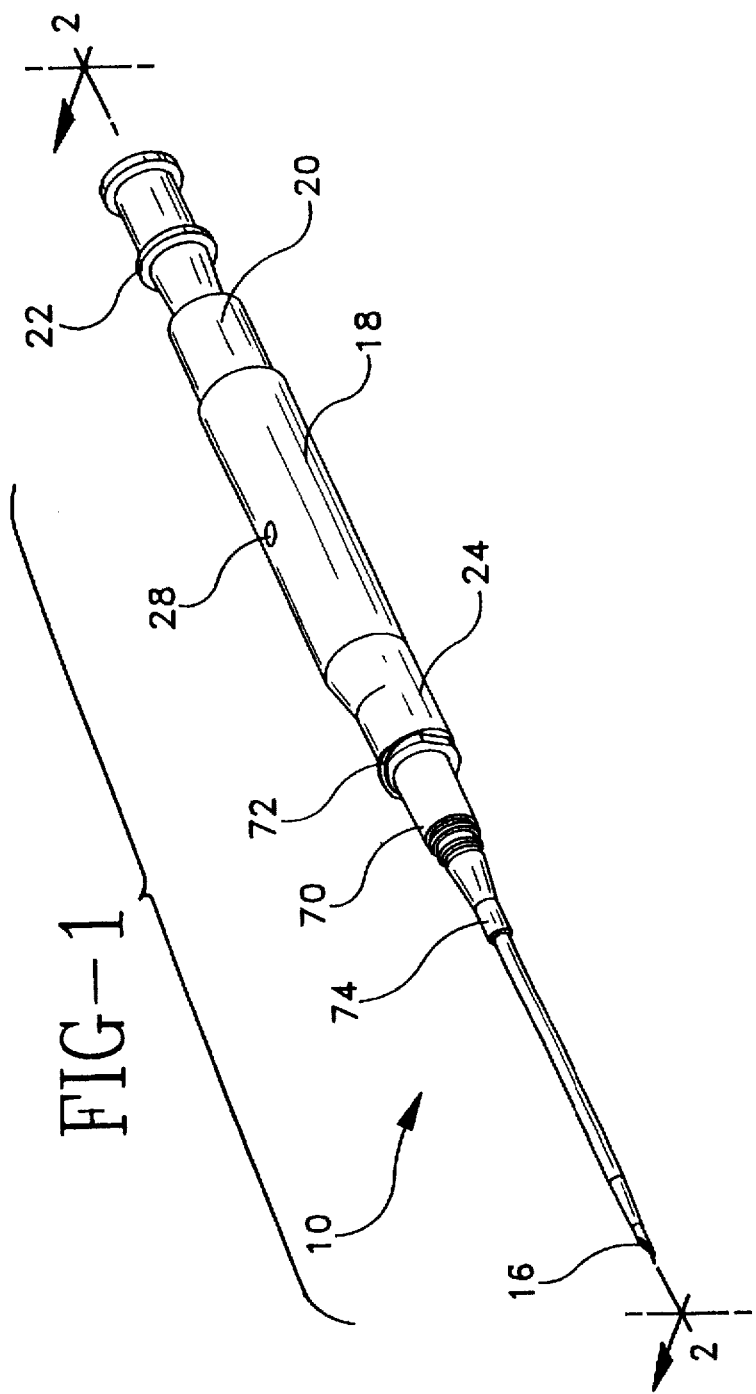
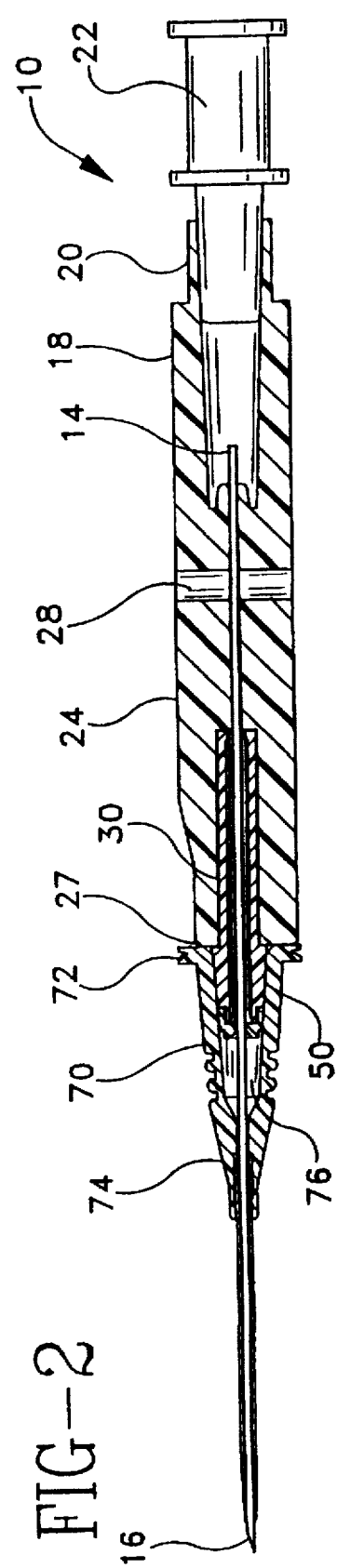

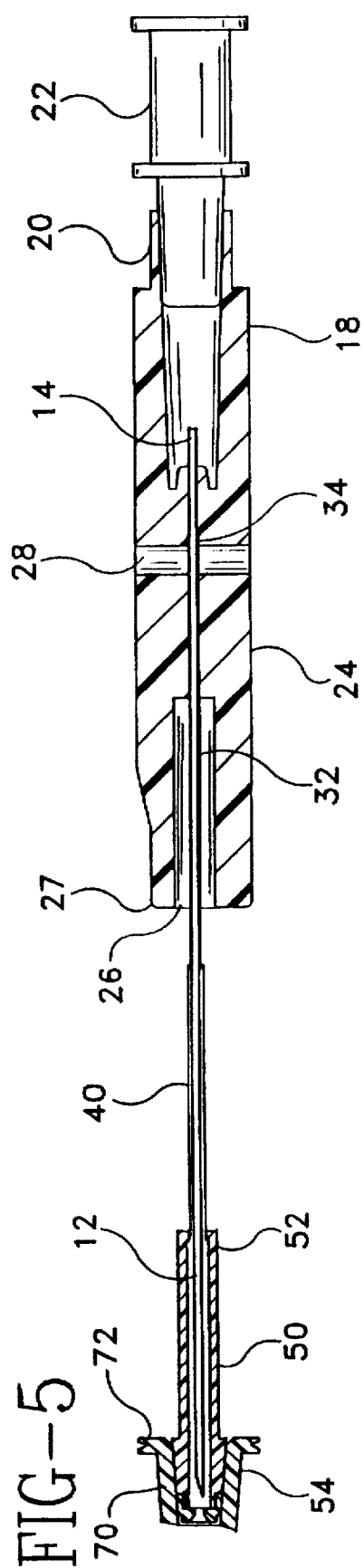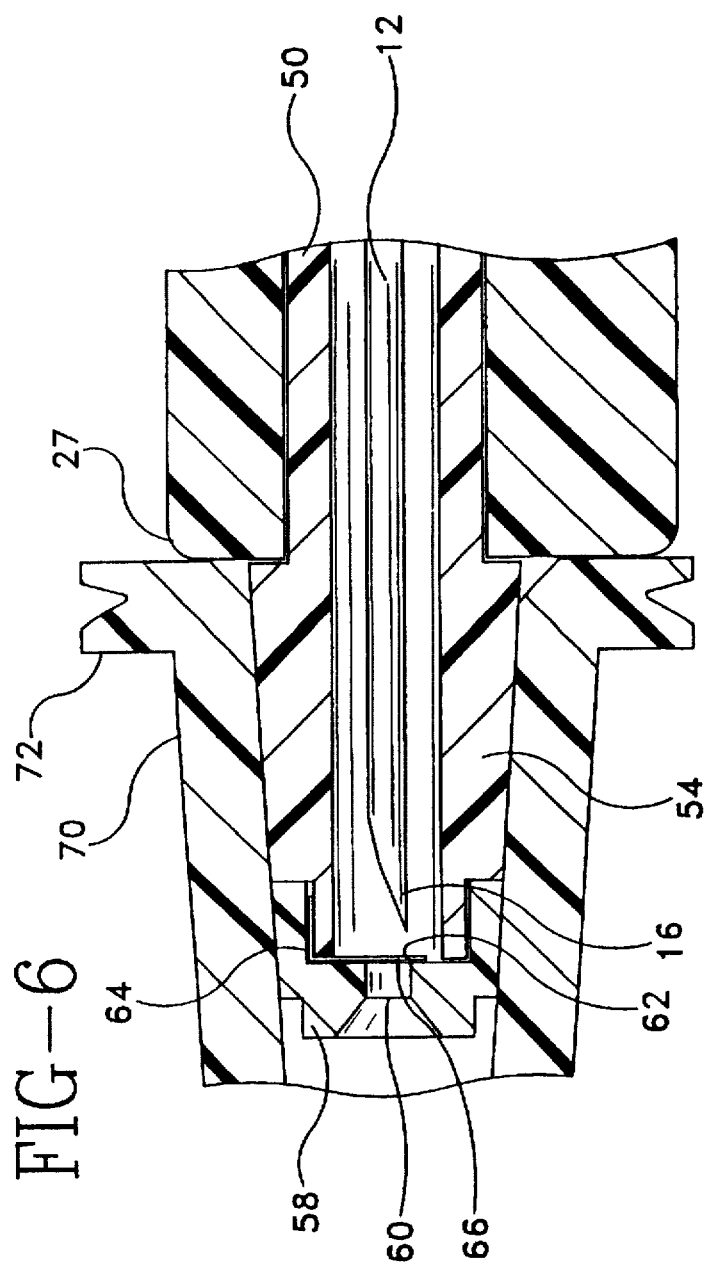

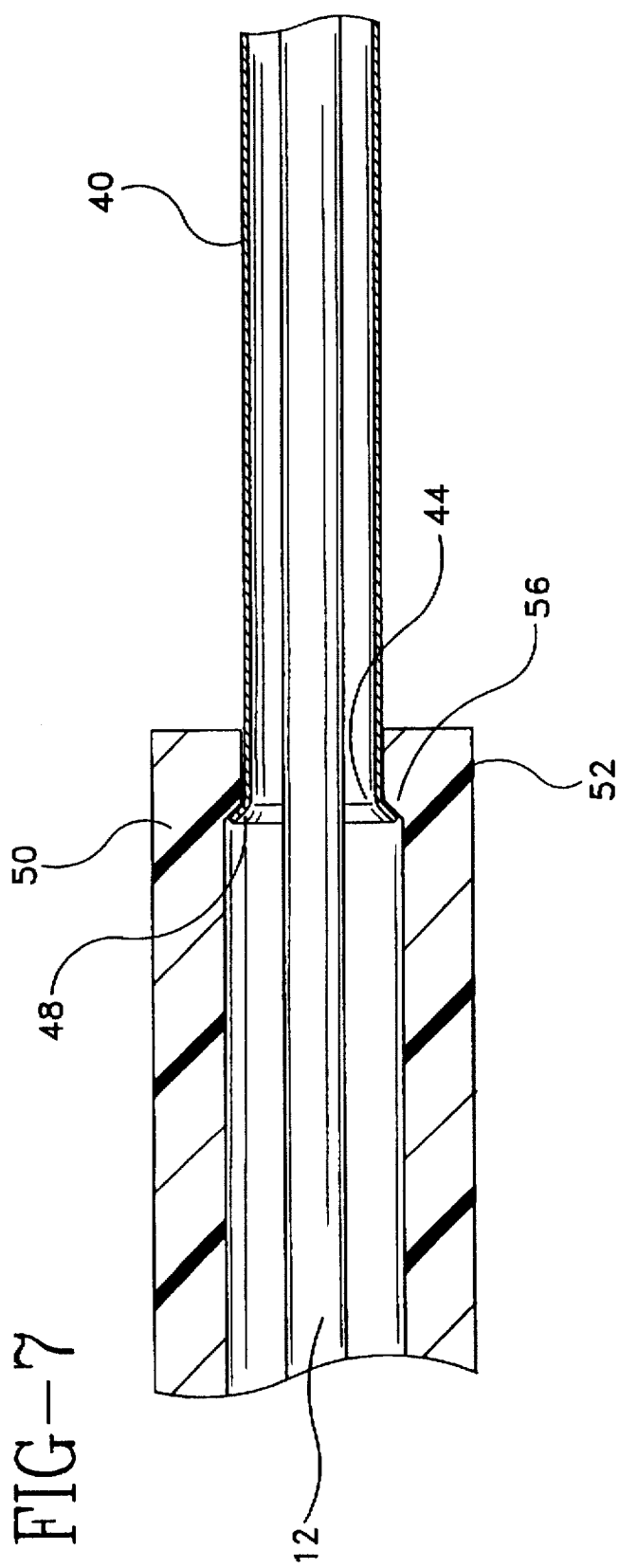
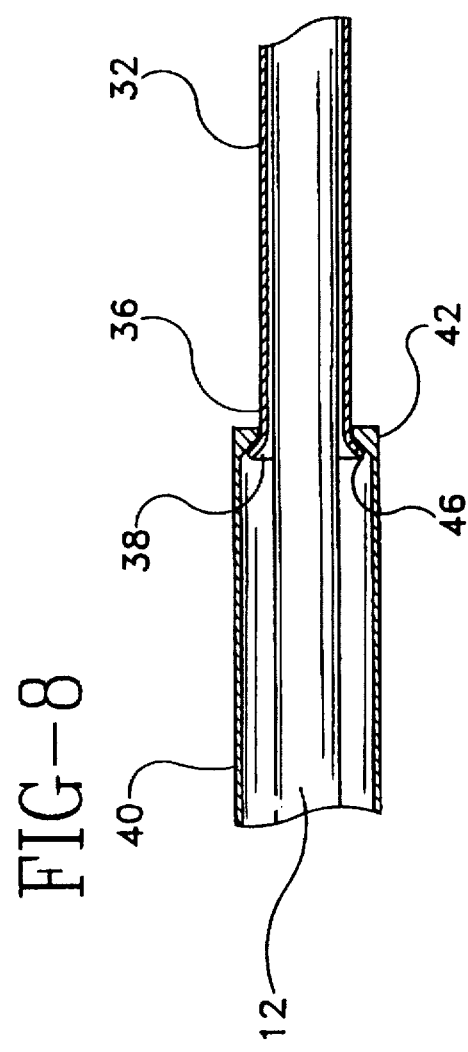

5,792,122

1

TELESCOPING NEEDLE SHIELD

This application is a continuation of application Ser. No. 08/682,479, filed Jul. 17, 1996 now abandoned which is a continuation of Ser. No. 08/501,604 filed Jul. 12, 1995 now abandoned.

BACKGROUND OF THE INVENTION

The subject invention relates to a needle point shield that will safely and automatically shield a needle after the needle has been used.

Sharp needles are typically used in health care procedures as part of a hypodermic needle assembly, a blood collection assembly or an intravenous (IV) catheter assembly. In recent years, there has been great concern over the immediate disposal of needles after use. This concern has arisen because of the advent of currently incurable and fatal diseases, such as Acquired Immune Deficiency Syndrome ("AIDS"), which can be transmitted by the exchange of body fluids from an infected person to another person. Thus, if a needle has been used to place a catheter in the vein to withdraw blood from or inject medicine into an AIDS infected person, the needle is a vehicle for the transmission of the disease. Thus, it is extremely important for a medical technician to properly dispose of the needle to avoid a needlestick with the-contaminated needle. Unfortunately, in certain medical environments, such as emergency situations or as a result of inattention or negligence, needlesticks with a contaminated needle still occur.

Some needle shields have already been designed. Some shields only cover the sharp distal tip of the needle. This is unsatisfactory in most instances because the shaft of the needle can be the source of contamination from body fluids. Thus, there still remains a need to provide a needle shield assembly that is simple and easy to use and that completely covers the entire needle after use.

SUMMARY OF THE INVENTION

It is therefore an object of this invention to provide a needle shield assembly that is simple and easy to use.

It is another object of this invention to provide a needle shield that completely covers the entire needle as well as the sharp distal tip of the needle after use.

Although this invention will be described in connection with a catheter introducer needle, it is to be understood that the shield assembly of this invention could be used with other needles where shielding of the needle is desirable.

The needle shield assembly of this invention includes a plurality of tubes concentrically overlapping one another, i.e. nested, and surrounding the needle. One tube in the shield assembly is securely affixed to the needle hub. Other tubes in the shield assembly can be telescoped distally relative to one another and relative to the needle hub. The tubes are dimensioned such that the shield assembly surrounds the distal tip of the needle when the tubes are telescopingly extended in a distal direction. Interlocking means prevents complete separation of the tubes from one another as they are extended distally. The distal-most tube of the extended shield assembly may include a tip guard securely mounted therein and biased against the needle. The tip guard will slide along the shaft of the needle as the tubes of the shield assembly are extended. After sufficient extension, the tip guard will pass distally beyond the distal tip of the needle, and will move toward an unbiased condition over the distal tip of the needle. Thus, the tip guard prevents proximal movement of the tubes or distal movement of the needle that could re-expose the distal tip of the used needle.

The tubes are thin-walled, but are sufficiently rigid to prevent kinking and to ensure smooth telescoping movement. The distal tubes can nest inside the proximal tubes or the distal tubes can nest outside the proximal tube. Where the distal tubes nest outside the proximal tubes, the outermost tube may be thicker than the others to protect and support the inner, thinner tubes. The thicker outer-most tube may be the tube that telescopes over the distal portion of the needle. Thus, this thicker outer tube provides accurate and efficient support for the above described tip guard therein. The outer-most tube may be releasably engaged with a catheter adapter. In this embodiment, the collapsed shield assembly is effectively enclosed between the needle hub and the catheter adapter.

After introduction of the catheter into the patient, the needle is removed from the patient in the conventional manner. This proximal movement of the needle hub and needle causes the tubes of the needle shield assembly to telescopingly extend relative to one another. Thus, the needle is gradually and automatically shielded as it is withdrawn from the patient and from the catheter adapter. After telescoping extension of the tubes in the shield assembly, the tip guard in the outer-most tube resiliently moves toward an unbiased condition over the distal tip of the needle. Further proximally directed forces on the needle hub will separate the outer-most tube from the catheter adaptor. Thus, the entire needle is safely shielded. Re-exposure of the needle by telescopingly collapsing the tubes is prevented by the tip guard. Additionally, re-exposure of the used needle by separating the telescoped tubes is prevented by the interlocking means between adjacent tubes. The shielded needle may be discarded in an appropriate receptacle and the catheter adapter may be placed in communication with other fittings and tubes as required.

BRIEF DESCRIPTION OF THE DRAWINGS

The preferred embodiments are illustrated in the drawings in which like reference numerals refer to like elements and in which:

FIG. 1 is a perspective view of the telescoping needle shield assembly of this invention;

FIG. 2 is a cross-sectional view of the telescoping needle shield assembly of FIG. 1;

FIG. 5 is a cross-sectional view of a portion of the telescoping needle shield of this invention showing the needle in a shielded condition prior to separation from the catheter adapter;

FIG. 6 is a cross-sectional view similar to FIG. 3, but showing the tip guard in an unbiased condition shielding the tip of the needle;

FIG. 7 is an enlarged cross-sectional view of a portion of the telescoping needle shield assembly of this invention showing the interlocking means between the outer and middle tubes;

FIG. 8 is an enlarged cross-sectional view of a portion of the telescoping needle shield assembly of this invention showing the interlocking means between the middle and inner tubes.

DETAILED DESCRIPTION OF THE INVENTION

Figure 3:
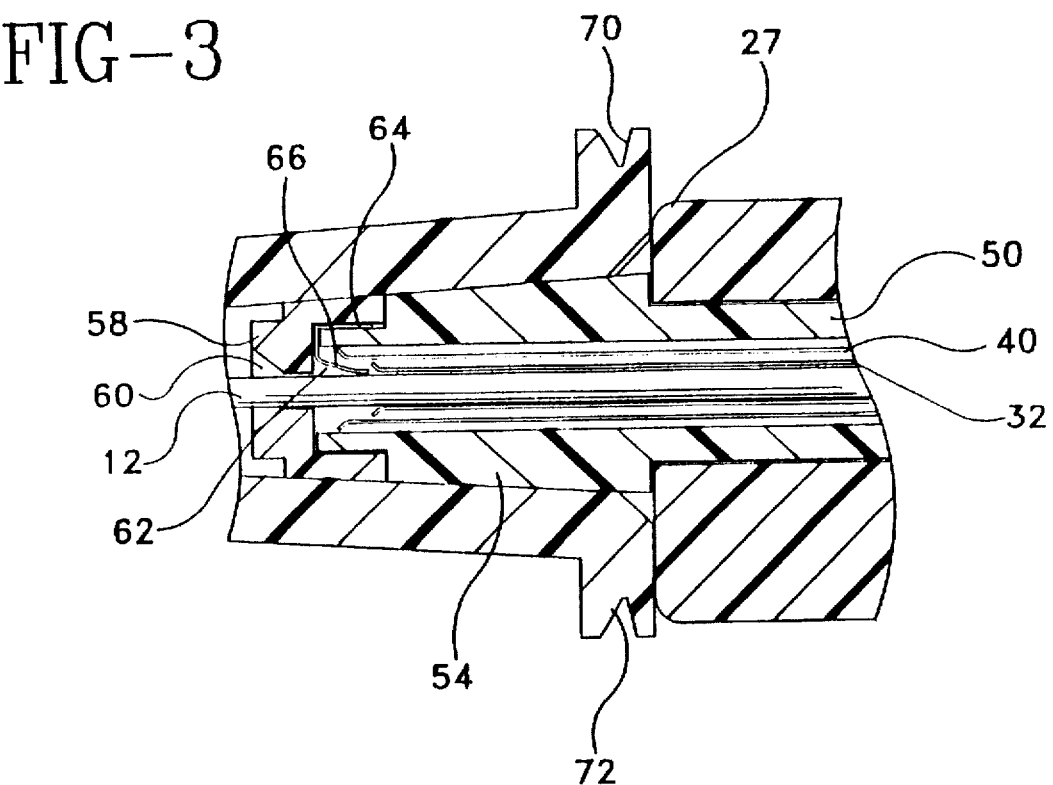
FIG. 3 is an enlarged cross-sectional view of a portion of the telescoping needle shield assembly of this invention showing the resilient tip guard biased against the shaft of the needle.
Figure 4:
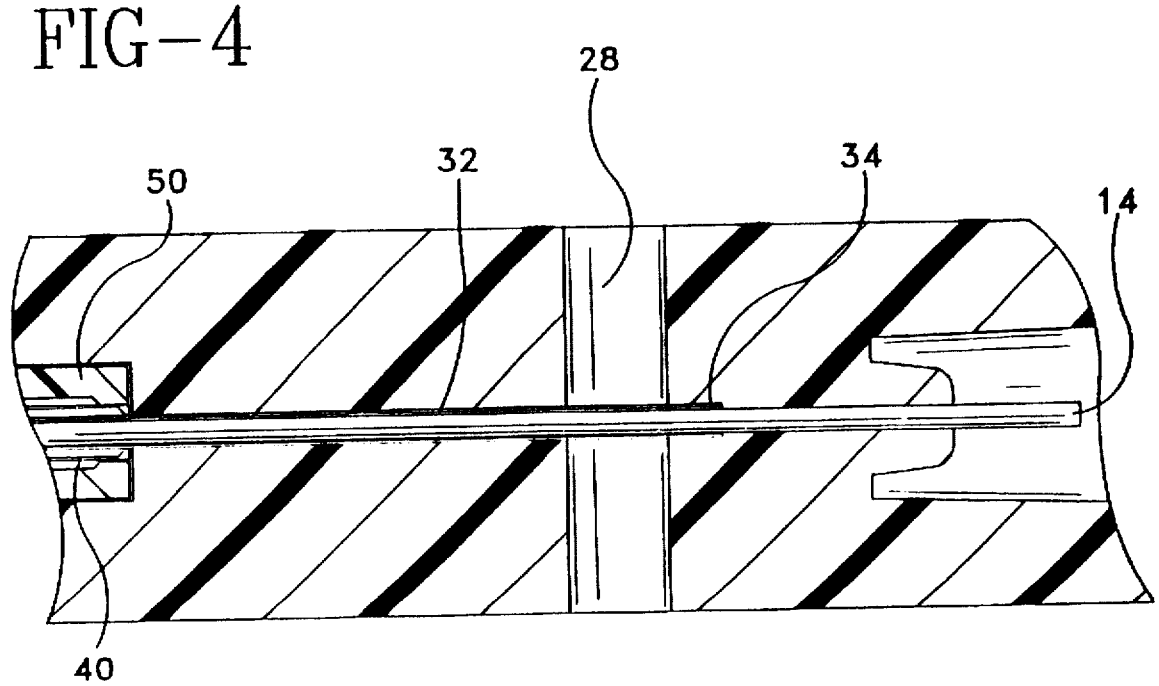
FIG. 4 is a cross-sectional view of a portion of the telescoping needle shield assembly of this invention showing the needle and inner-most tube secured to the needle hub.

A needle shield assembly in accordance with the subject invention is identified generally by the numeral 10 in FIGS. 1-9. Assembly 10 includes a needle 12 having a proximal end 14, an opposed sharply pointed distal end 16 and a lumen extending therebetween.

Proximal end 14 of needle 12 is securely adhered in a needle hub 18 in the standard manner using a sidehole glue port in hub 18. (Not shown.) Hub 18 includes a proximal end 20 which extends proximally beyond proximal end 14 of needle 12 to define a flash chamber. A vent plug 22 is mounted to proximal end 20 of needle hub 18 to seal the flash chamber.

Hub 18 further includes a distal end 24 which extends to a location intermediate proximal and distal ends 14 and 16 of needle 12. A shield cavity 26 extends proximally into distal end 24 of hub 18 to end 27, and is radially dimensioned to receive a shield as explained further herein. A glue port 28 extends diametrically through needle hub 18 at a location proximally of shield cavity 26.

A telescoping shield assembly 30 is mounted concentrically around needle 12 and is initially disposed substantially within shield cavity 26. Shield assembly 30 includes a tubular base shield 32 having a proximal end 34 projecting proximally into needle hub 18 beyond shield cavity 26 and proximally beyond glue port 28. Base shield 32 further includes a distal end 36, which, in the embodiments shown herein, projects distally beyond hub 18. Distal end 36 of base shield 32 includes an outwardly extending locking flange 38 for cooperatively locking with another of the telescoped shield members as explained further herein.

Shield assembly 30 further includes a tubular intermediate shield 40 telescoped over base shield 32. Intermediate shield 40 includes opposed proximal and distal ends 42 and 44 respectively. In the collapsed condition of shield assembly 30 depicted in FIG. 2, proximal end 42 of intermediate shield 40 is near distal end 27 of shield cavity 26 in needle hub 18. However, intermediate shield 40 can be slid distally relative to base shield 32 and into the position shown in FIG. 5. Proximal end 42 of intermediate shield 40 includes an inwardly extending locking flange 46 which is dimensioned to engage outwardly extending locking flange 38 of base shield 32 for preventing complete separation. See FIG. 8. Distal end 44 of intermediate flange 40 includes an outwardly extending locking flange 48. See FIG. 7.

Base shield 32 and intermediate shield 40 have thicknesses selected to prevent kinking during a shielding operation, and to ensure smooth telescoping movement. However, neither base shield 32 nor intermediate shield 40 will directly contact sharply pointed distal tip 16 of needle 12, and hence a small thickness is acceptable. Preferably stainless steel is used as the material. A wall thickness in the range of 0.002 inches to 0.007 inches is preferred for base shield 32 and intermediate shield 40.

Shield assembly 30 further includes a shield housing 50 slidably telescoped over intermediate shield 40. Shield housing 50 includes a proximal end 52 and an opposed distal end 54. In the collapsed condition of shield assembly, as shown in FIG. 2, proximal end 52 of shield housing 50 is near distal end 27 of shield cavity 26. However, shield housing 50 can be slid distally and into the position shown in FIG. 5. Proximal end 52 includes an inwardly extending locking flange 56 for lockingly engaging outwardly extending locking flange 48 of intermediate shield 40 to prevent complete separation. See FIG. 7. Shield housing 50 defines a wall thickness substantially greater than the wall thicknesses of base shield 32 and intermediate shield 40. Preferably shield housing 50 should have a wall thickness of at least about 5 times the wall thickness of base shield 32 and intermediate shield 40. This greater wall thickness is provided for several reasons. First, shield housing 50 surrounds both base shield 32 and intermediate shield 40 in the collapsed condition of the shield assembly. The greater wall thickness for shield housing 50 protects the thinner base shield 32 and intermediate shield 40 during periods of storage, shipment and initial use of needle assembly 10. Additionally, in the extended condition of shield assembly 30, as explained in greater detail below, shield housing 50 will be in proximity to sharply pointed distal end 16 of needle 12. Hence, the greater wall thickness of shield housing 50 provides added protection against puncture. Although this invention is described with the distal tubes nested outside the proximal tubes, it is to be understood that the distal tubes could be nested inside the proximal tubes.

Figure 9:
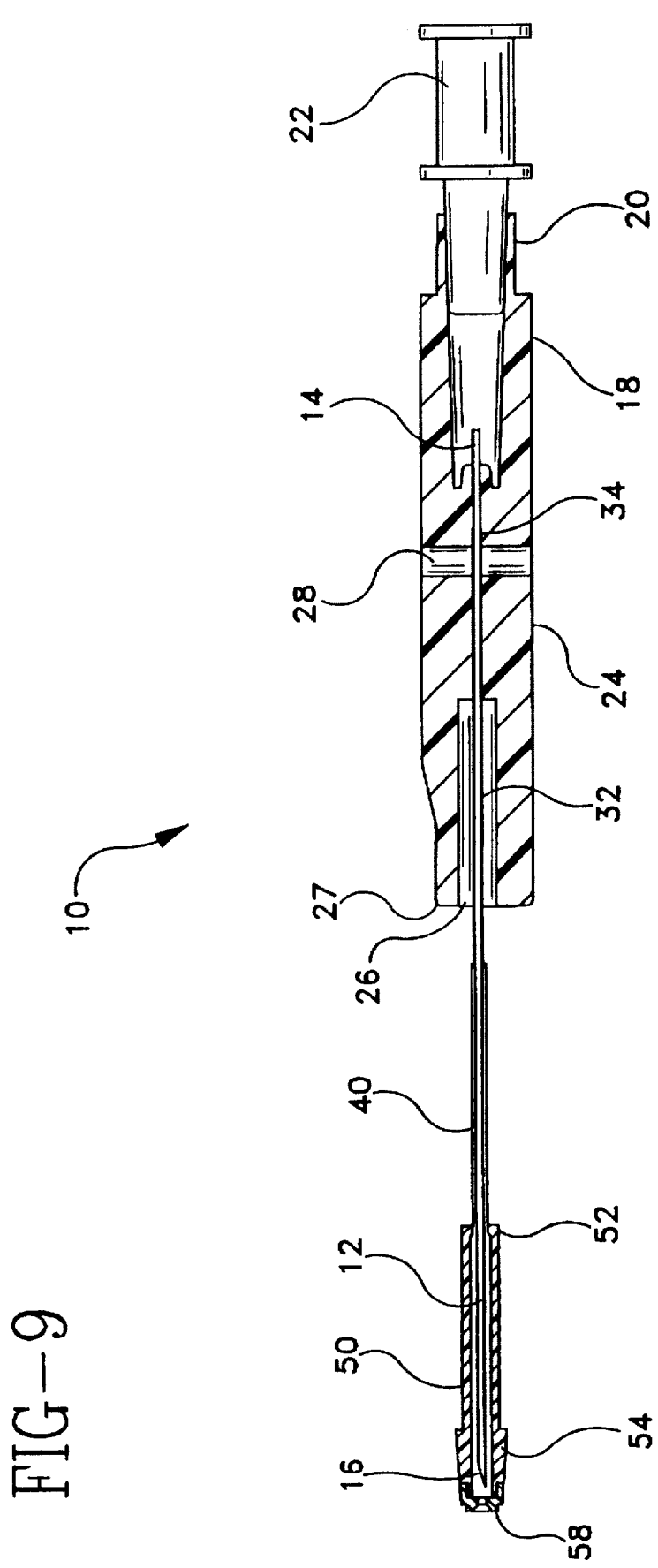
FIG. 9 is a cross-sectional view of the telescoping needle shield assembly of this invention shielding the needle after separation from the catheter adapter.

Base shield 32, intermediate shield 40 and shield housing 50 define respective lengths to have their distal ends 36, 44 and 54 approximately aligned in the collapsed condition of shield assembly 30 shown in FIG. 3. Furthermore, distal ends 36, 44 and 54 will project only a small distance distally beyond needle hub 18, and will terminate a significant distance proximally of distal end 16 of needle 12 in the collapsed condition of shield assembly 30 shown in FIG. 2. However, the lengths of base shield 32, intermediate shield 40 and shield housing 50 are selected to ensure that shield housing 50 extends distally beyond distal end 16 of needle 12 in the extended condition of shield assembly 30 as depicted in FIGS. 5 and 9. The lengths for base shield 32, intermediate shield 40 and shield housing 50 depend on the length of needle 12 to be shielded. It is to be understood that three telescoping tubes are preferable. However, additional telescoping tubes or even fewer telescoping tubes could be used for different length needles.

Shield assembly 30 further includes a shield housing cap 58 securely engaged over distal end 54 of shield housing 50. Shield housing cap 58 includes a central aperture 60 extending therethrough which is dimensioned for slidable movement along needle 12.

As shown most clearly in FIGS. 3 and 6, a tip guard 62 is securely mounted between distal end 54 of shield housing 50 and shield housing cap 58. Tip guard 62 is formed from a resilient material, preferably a stainless steel shim, and includes a mounting leg 64 securely engaged between shield housing 50 and shield housing cap 58. Tip guard 62 also includes a shielding leg 66. Shielding leg 66 is biased away from mounting leg 64 generally perpendicular thereto. In the collapsed condition of needle shield assembly 10, shielding leg is moved to a position generally parallel to mounting leg 64 into sliding engagement with the shaft of needle 12.

Needle shield assembly 10 is preferably used in conjunction with an IV catheter to introduce the catheter into a patient. The catheter includes a catheter adapter 70 having a proximal end 72, a tapered distal end 74 and a lumen 76 extending therebetween. Portions of lumen 76 extending distally from proximal end 72 are dimensioned to achieve a slight interference fit over shield housing cap 58 and over a distal portion of shield housing 50. More distal portions of lumen 76 are dimensioned to slidably surround needle 12.

Needle shield assembly 10 is used by initially introducing distal end 16 of needle 12 into a patient. Needle shield assembly 10 is advanced a sufficient distance distally into the patient for the distal end of the catheter to enter the patient's vein. Upon proper positioning of the catheter in the patient's vein, a health care worker using needle shield assembly 10 will exert proximally directed forces on needle hub 18 while holding catheter adapter 70 substantially in place. These initial proximally directed forces will cause a is proximal movement of needle 12 and hub 18 and will cause a telescoping of shield assembly 30. More particularly, as noted above, proximal end 14 of needle 12 is adhered to needle hub 18 and proximal end 34 of base shield 32 is secured to needle hub 18 at glue port 28. Thus, the initial proximal movement of hub 18 will simultaneously draw needle 12 and base shield 32 in a proximal direction.

Sufficient proximal movement of needle 12, needle hub 18 and base shield 32 will cause outwardly extending locking flange 38 at distal end 36 of base shield 32 to engage inwardly extending locking flange 46 at proximal end 42 of intermediate shield 40. Hence, further proximal movement of base shield 32 will effectively pull intermediate shield 40 relative to shield housing 50. The interference fit between catheter adapter 70 and shield housing cap 58 and shield housing 50 must provide frictional forces greater than the amount of the proximally directed force needed to extend needle shield assembly 10 to prevent shield housing 50 from prematurely disengaging from catheter adapter 70.

Further proximal movement of hub 18 causes locking flange 48 on distal end 44 of intermediate shield 40 to engage inwardly extending locking flange 56 at proximal end 52 of shield housing 50 and prevents further relative movement between intermediate shield 40 and shield housing 50. As needle 12 is moved further in a proximal direction, distal tip 16 thereof will move proximally of shielding leg 66 of tip guard 62. Hence, shielding leg 66 will resiliently move toward an undeflected condition and will safely cover pointed distal end 16 of needle 12 as shown in FIG. 6. Thus, any distal movement of needle 12 relative to shield assembly 30 that could conceivably re-expose needle 12 is prevented.

Extension of shield assembly 30 beyond the FIG. 6 condition is prevented by engagement of the locking flanges as explained above. Hence, further proximally directed forces on needle hub 18 will overcome the interference fit between shield housing 50 and catheter adapter 70. Thus, as shown in FIG. 9, shield housing 50 and shield housing cap 54 will slidably separate from catheter adapter 70. In this separated condition, all portions of needle 12 projecting beyond needle hub 18 are safely surrounded and shielded. Additionally, tip guard 62 is disposed distally of distal end 16 of needle 12 to prevent any possible re-exposure of needle 12. Furthermore, the relatively great thickness of shield housing 50 substantially prevents any possibility of puncture by distal end 16 of needle 12. The shielded needle may be safely and appropriately discarded in an appropriate receptacle. Catheter adapter 70 may then be connected to an appropriate IV tube for use in the conventional manner.

Thus, it is seen that a needle shield assembly is provided that is simple and easy to use and that completely covers the entire needle as well as the sharp distal tip after use.

We claim:

1. A needle shield for a needle having opposed proximal and distal ends, said shield comprising a plurality of tubes surrounding said needle, with a proximal-most tube defining a base tube fixed in proximity to said proximal end of said needle, and a distal-most tube operably connected to the base tube for telescoping movement between a collapsed condition where the distal-most tube is disposed over the base tube and the distal end of said needle is exposed and an extended condition where the distal end of the needle is surrounded by the shield and wherein the distal-most tube has a wall thickness greater than a wall thickness of the base tube.

2. The needle shield of claim 1, wherein said tubes are movingly interlocked with one another for preventing complete separation during said telescoping movement of said tubes toward said extended condition.

3. The needle shield of claim 2, wherein the distal-most tube further includes a tip guard for covering the distal end of said needle in the extended condition of the tubes.

4. The needle shield of claim 3, wherein the tip guard comprises a member disposed and configured for sliding movement against the needle during the telescoping movement of the tubes from the collapsed condition toward the extended condition and being disposed to move over the distal end of the needle when the tubes are telescopingly moved to the extended condition.

5. A catheter introducer set, comprising:
   a needle having opposed proximal and distal ends;
   a needle hub securely connected to the proximal end of the needle, portions of the needle hub intermediate the proximal and distal ends of the needle defining a shield cavity surrounding the needle;
   a shield assembly surrounding the needle and comprising a plurality of nested tubes in sliding telescoping relation with one another with a proximal-most tube defining a base tube having a proximal end secured to the needle hub and a distal-most tube operably connected to the base tube wherein the distal-most tube has a wall thickness greater than a wall thickness of the base tube and the distal-most tube is disposed over the base tube when the shield assembly is in a collapsed condition; and
   a catheter adapter, the shield assembly being releasably engaged with the catheter adapter.

6. The catheter introducer set of claim 5 further comprising a lock to prevent separation of the tubes from one another during telescoping movement therebetween.

7. The catheter introducer set of claim 6 further comprising a tip guard connected to the distal-most tube to prevent distal movement of the needle beyond the shield assembly once the needle has been withdrawn into the shield assembly.

8. The catheter introducer set of claim 5 further including a locking mechanism to prevent separation of the plurality of nested tubes from one another.

9. The catheter introducer set of claim 8 wherein the distal-most tube includes a tip guard to prevent distal movement of the needle with respect to the distal-most tube after the needle has been completely withdrawn inside the distal-most tube.

10. The catheter introducer set of claim 5, further comprising a metallic tip guard mounted in the distal-most tube and being slidable along the needle as the shield assembly is moved toward the extended condition, the tip guard being biased to move over the distal end of the needle when the shield assembly slidably telescopes into the extended condition.

11. The needle shield of claim 1 wherein the wall thickness of the distal-most tube is at least about 5 times the wall thickness of the base tube.

12. The catheter introducer set of claim 5 wherein the wall thickness of the distal-most tube is at least about 5 times the wall thickness of the base tube.

13. The needle shield of claim 1 wherein the wall thickness of the base tube is between 0.002 inches to 0.007 inches.

14. The catheter introducer set of claim 5 wherein the wall thickness of the base tube is between 0.002 inches to 0.007 inches.

* * * * *